United States Patent
Colon et al.

(10) Patent No.: US 11,440,808 B2
(45) Date of Patent: Sep. 13, 2022

(54) AMMONIA SYNTHESIS METHODS AND SYSTEMS

(71) Applicant: President and Fellows of Harvard College, Cambridge, MA (US)

(72) Inventors: Brendan Cruz Colon, Cambridge, MA (US); Chong Liu, Cambridge, MA (US); Daniel G. Nocera, Winchester, MA (US); Pamela Ann Silver, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 679 days.

(21) Appl. No.: 16/314,979

(22) PCT Filed: Jun. 14, 2017

(86) PCT No.: PCT/US2017/037447
§ 371 (c)(1),
(2) Date: Jan. 3, 2019

(87) PCT Pub. No.: WO2018/009315
PCT Pub. Date: Jan. 11, 2018

(65) Prior Publication Data
US 2019/0202707 A1    Jul. 4, 2019

Related U.S. Application Data

(60) Provisional application No. 62/358,710, filed on Jul. 6, 2016.

(51) Int. Cl.
*C01C 1/08*     (2006.01)
*C01C 1/04*     (2006.01)
(Continued)

(52) U.S. Cl.
CPC ............... *C01C 1/08* (2013.01); *B01J 19/087* (2013.01); *C01C 1/04* (2013.01); *C12P 3/00* (2013.01);
(Continued)

(58) Field of Classification Search
CPC .. C01C 1/02; C01C 1/04; C01C 1/045; C01C 1/08; C01C 1/083; C01C 1/086;
(Continued)

(56) References Cited

U.S. PATENT DOCUMENTS 3,560,344 A    2/1971   Bulen
4,798,662 A    1/1989   Clerc-Renaud et al.
(Continued)

FOREIGN PATENT DOCUMENTS

CN        103237599 A    8/2013
JP         2005-505419 T   2/2005
(Continued)

OTHER PUBLICATIONS

Liu et al, "Water splitting-biosynthetic system with CO2 reduction efficiencies exceeding photosynthesis" Science, 2016, p. 1210-2013. (Year: 2016).*
(Continued)

*Primary Examiner* — Anthony J Zimmer
(74) *Attorney, Agent, or Firm* — Wolf, Greenfield & Sacks, P.C.

(57) ABSTRACT

Systems and methods for producing ammonia are described. In one embodiment, hydrogen, carbon dioxide, and nitrogen are dissolved in a solution. A glutamine synthetase inhibitor and autotrophic diazotroph bacteria are also placed in the solution.

8 Claims, 6 Drawing Sheets

(51) Int. Cl.
  *C12P 3/00* (2006.01)
  *C25B 11/061* (2021.01)
  *B01J 19/08* (2006.01)
  *C25B 1/04* (2021.01)

(52) U.S. Cl.
  CPC .............. *C25B 1/04* (2013.01); *C25B 11/061* (2021.01); *B01J 2219/00761* (2013.01)

(58) Field of Classification Search
  CPC . C12P 3/00; C12N 1/20; C25B 11/061; C25B 1/04; B01J 19/087; B01J 2219/00761; Y02E 60/36
  See application file for complete search history.

(56) References Cited

U.S. PATENT DOCUMENTS

| | | | |
|---|---|---|---|
| 10,597,681 | B2 | 3/2020 | Colon et al. |
| 11,091,781 | B2 | 8/2021 | Colon et al. |
| 2003/0010076 | A1 | 1/2003 | Stewart |
| 2004/0089042 | A1 | 5/2004 | Henderson |
| 2010/0101955 | A1 | 4/2010 | Nocera et al. |
| 2010/0234222 | A1 | 9/2010 | Gidekel et al. |
| 2011/0104037 | A1 | 5/2011 | Stahl et al. |
| 2011/0277991 | A1 | 11/2011 | Toledo et al. |
| 2012/0061237 | A1 | 3/2012 | Brichese et al. |
| 2013/0130341 | A1 | 5/2013 | Liao et al. |
| 2013/0189763 | A1 | 6/2013 | Dalla-Betta et al. |
| 2013/0219560 | A1 | 8/2013 | Sayre |
| 2014/0017161 | A1 | 1/2014 | Andrews et al. |
| 2014/0179942 | A1 | 6/2014 | Finnegan |
| 2014/0346108 | A1* | 11/2014 | Josse ................ C02F 11/12 210/605 |
| 2014/0377857 | A1 | 12/2014 | Liao et al. |
| 2015/0176030 | A1 | 6/2015 | Wolfowitz |
| 2015/0176033 | A1 | 6/2015 | Conner et al. |
| 2015/0225750 | A1 | 8/2015 | Yi-Xin et al. |
| 2016/0046964 | A1 | 2/2016 | Ward et al. |
| 2016/0102287 | A1 | 4/2016 | Dalla-Betta et al. |
| 2016/0199821 | A1 | 7/2016 | Sung et al. |
| 2016/0289130 | A1 | 10/2016 | Innes et al. |
| 2017/0080446 | A1 | 3/2017 | Roller et al. |
| 2018/0265898 | A1* | 9/2018 | Colon ................ C25B 15/08 |
| 2019/0202707 | A1 | 7/2019 | Colon et al. |
| 2020/0102254 | A1 | 4/2020 | Sakimoto et al. |

FOREIGN PATENT DOCUMENTS

| | | |
|---|---|---|
| JP | 2016-106637 A | 6/2016 |
| WO | WO 03/033418 | 4/2003 |
| WO | WO 2010/142004 A2 | 12/2010 |
| WO | WO 2011/100732 A2 | 8/2011 |
| WO | WO 2013/123454 A1 | 8/2013 |
| WO | WO 2017/048773 | 3/2017 |
| WO | WO 2018/009315 A1 | 1/2018 |
| WO | WO 2018/213568 A1 | 11/2018 |

OTHER PUBLICATIONS

Supplemental Material for Liu et al., "Water splitting-biosynthetic system with CO2 reduction efficiencies exceeding photosynthesis" Science, 2016, p. 1210-2013. (Year: 2016).*
Shokri et al., "Ammonium Production During the Nitrogen-Fixing Process by Wild Paenibacillus Strains and Cell-Free Extract Adsorbed on Nano TiO2 Particles," J. Microbiol. Biotechnol. (2010), 20(8), 1251-1258. (Year: 2010).*
Colnaghi et al., "Strategies for increased ammonium production in free-living or plant associated nitrogen fixing bacteria," Plant and Soil 194: 145-154, 1997. (Year: 1997).*
U.S. Appl. No. 16/614,133, filed Nov. 15, 2019, Sakimoto et al.
Office Action for Application No. 201680066308.3 dated May 5, 2019.
Office Action for Application No. 201680066308.3 dated Dec. 6, 2019.
International Search Report and Written Opinion for Application No. PCT/US2016/051621 dated Dec. 1, 2016.
International Preliminary Report on Patentability for Application No. PCT/US2016/051621 dated Mar. 29, 2018.
Extended European Search Report dated Jan. 7, 2020 for Application No. EP 17824683.1.
Supplementary European Search Report dated Jan. 24, 2020 for Application No. EP 17824683.1.
European Office Action dated Nov. 13, 2020 for Application No. EP 17824683.1.
Japanese Office Action dated Mar. 15, 2021 for Application No. 2018-568227.
International Search Report and Written Opinion for Application No. PCT/US2017/037447 dated Aug. 14, 2017.
International Preliminary Report on Patentability for Application No. PCT/US2017/037447 dated Jan. 17, 2019.
Invitation to Pay Additional Fees for Application No. PCT/US2018/033170 dated Jul. 13, 2018.
International Search Report and Written Opinion for Application No. PCT/US2018/033170 dated Sep. 19, 2018.
International Preliminary Report on Patentability for Application No. PCT/US2018/033170 dated Nov. 28, 2019.
Ali et al., Nanostructured photoelectrochemical solar cell for nitrogen reduction using plasmon-enhanced black silicon. Nat Commun. Apr. 20, 2016;7:11335. doi:10.1038/ncomms11335.
Anderson et al., Catalytic conversion of nitrogen to ammonia by an iron model complex. Nature. Sep. 5, 2013;501(7465):84-7. doi: 10.1038/nature12435.
Arashiba et al., A molybdenum complex bearing PNP-type pincer ligands leads to the catalytic reduction of dinitrogen into ammonia. Nat Chem. Feb. 2011;3(2):120-5. doi: 10.1038/nchem.906. Epub Dec. 5, 2010.
Bediako et al., Catalytic Oxygen Evolution by Cobalt Oxido Thin Films. Top Curr Chem. 2016;371:173-213. doi: 10.1007/128_2015_649.
Berndt et al., The nitrogen-fixing system of Corynebacterium autotrophicum. Purification and properties of the nitrogenase components and two ferredoxins. Eur J Biochem. May 1978;86(1):133-42.
Brown et al., Light-driven dinitrogen reduction catalyzed by a CdS:nitrogenase MoFe protein biohybrid. Science. Apr. 22, 2016;352(6284):448-50. doi: 10.1126/science.aaf2091.
Carvalho et al., Nitrogen signalling in plant interactions with associative and endophytic diazotrophic bacteria. J Exp Bot. Oct. 2014;65(19):5631-42. doi: 10.1093/jxb/eru319. Epub Aug. 11, 2014.
Chaparro et al., Manipulating the soil microbiome to increase soil health and plant fertility. Biol Fertil Soils. 2012; 48:489-499 https://doi.org/10.1007/s00374-012-0691-4.
Danyal et al., Uncoupling nitrogenase: catalytic reduction of hydrazine to ammonia by a MoFe protein in the absence of Fe protein-ATP. J Am Chem Soc. Sep. 29, 2010;132(38):13197-9. doi: 10.1021/ja1067178.
Dixon, et al., Genetic regulation of biological nitrogen fixation. Nat Rev Microbiol. Aug. 2004;2(8):621-31. Review.
Drueckes et al., Photometric microtiter assay of inorganic phosphate in the presence of acid-labile organic phosphates. Anal Biochem. Sep. 1, 1995;230(1):173-7.
Ferguson ATP synthase: from sequence to ring size to the P/O ratio. Proc Natl Acad Sci U S A. Sep. 28, 2010;107(39):16755-6. doi: 10.1073/pnas.1012260107. Epub Sep. 21, 2010.
Gill et al.,The crystal structure of phosphinothricin in the active site of glutamine synthetase illuminates the mechanism of enzymatic inhibition. Biochemistry. Feb. 20, 2001;40(7):1903-12.
Grosz et al., Statistical mechanical estimation of the free energy of formation of *E. coli* biomass for use with macroscopic bioreactor balances. Biotechnol Bioeng. Sep. 1983;25(9):2149-63.
Guth et al., Inhibition of nitrogenase-catalyzed NH3 formation by H2. Biochemistry. Oct. 25, 1983;22(22):5111-22.
Hanford, Advanced Life Support Baseline Values and Assumptions Document doi: CTSD-ADV-484 A. (2006). Technical Reports. Paper 3. http://docs.lib.purdue.edU/nasatr/3.

(56) References Cited

OTHER PUBLICATIONS

Heinonen-Tanski et al., Human excreta for plant production. Bioresour Technol. Mar. 2005;96(4):403-11.

Hoffman et al., Mechanism of nitrogen fixation by nitrogenase: the next stage. Chem Rev. Apr. 23, 2014;114(8):4041-62. doi: 10.1021/cr400641x. Epub Jan. 27, 2014.

Hoops et al., COPASI—a COmplex PAthway Simulator. Bioinformatics. Dec. 15, 2006;22(24):3067-74. Epub Oct. 10, 2006.

Kandler et al., Occurrence of Poly-γ-D -Glutamic Acid and Poly-α-L-Glutamine in the Genera Xanthobacter, Flexithrix, Sporosarcina and Pianococcus. Syst Appl Microbiol. 1983;4(1):34-41. doi:10.1016/S0723-2020(83)80032-0.

Kramer et al., Variable use of plant and soil derived carbon by microorganisms in agricultural soils. Soil Biol Biochem. 2006; 38:3267-3278. https://doi.org/10.1016/j.soilbio.2006.04.006.

Kuriyama et al., Catalytic formation of ammonia from molecular dinitrogen by use of dinitrogen-bridged dimolybdenum-dinitrogen complexes bearing PNP-pincer ligands: remarkable effect of substituent at PNP-pincer ligand. J Am Chem Soc. Jul. 9, 2014;136(27):9719-31. doi: 10.1021/ja5044243. Epub Jun. 25, 2014.

Lan et al., Synthesis of ammonia directly from air and water at ambient temperature and pressure. Sci Rep. 2013;3:1145. doi: 10.1038/srep01145. Epub Jan. 29, 2013.

Langmead et al., Fast gapped-read alignment with Bowtie 2. Nat Methods. Mar. 4, 2012;9(4):357-9. doi: 10.1038/nmeth.1923.

Li et al., Efficient Visible Light Nitrogen Fixation with BiOBr Nanosheets of Oxygen Vacancies on the Exposed {001} Facets. J Am Chem Soc. May 20, 2015;137(19):6393-9. doi: 10.1021/jacs.5b03105. Epub May 3, 2015. Erratum in: J Am Chem Soc. Jan. 10, 2018;140(1):526. Epub May 3, 2015.

Li et al., The Sequence Alignment/Map format and SAMtools. Bioinformatics. Aug. 15, 2009;25(16):2078-9. doi: 10.1093/bioinformatics/btp352. Epub Jun. 8, 2009.

Liu et al., Ambient nitrogen reduction cycle using a hybrid inorganic-biological system. Proc Natl Acad Sci U S A. Jun. 20, 2017;114(25):6450-6455.

Liu et al., Nitrogenase-mimic iron-containing chalcogels for photochemical reduction of dinitrogen to ammonia. Proc Natl Acad Sci U S A. May 17, 2016;113(20):5530-5. doi: 10.1073/pnas.1605512113. Epub May 2, 2016.

Liu et al., Water splitting-biosynthetic system with $CO_2$ reduction efficiencies exceeding photosynthesis. Science. Jun. 3, 2016;352(6290):1210-3.

Mader et al., Soil fertility and biodiversity in organic farming. Science. May 31, 2002;296(5573):1694-7.

Mahmood et al., Seed biopriming with plant growth promoting rhizobacteria: a review. FEMS Microbiol Ecol. Aug. 2016;92(8). pii:fiw112. doi: 10.1093/femsec/fiw112. Epub May 23, 2016.

Malik et al., Enrichment and isolation of nitrogen fixing hydrogen bacteria. Arch Microbiol. Mar. 19, 1976;107(2):139-42.

Miflin et al. The role of glutamine synthetase and glutamate dehydrogenase in nitrogen assimilation and possibilities for improvement in the nitrogen utilization of crops. J Exp Bot. Apr. 2002;53(370):979-87.

Milton et al., Nitrogenase bioelectrocatalysis: heterogeneous ammonia and hydrogen production by MoFe protein. 2016. Energy Environ Sci 9: 2550-2554. DOI: 10.1039/c6ee01432a.

Murrell et al., M.E. Arch. Microbiol. (1983) 136: 219. https://doi.org/10.1007/BF00409848.

Nocera, The artificial leaf. Acc Chem Res. May 15, 2012;45(5):767-76. doi: 10.1021/ar2003013. Epub Apr. 4, 2012.

Ortiz-Marques et al., Metabolic engineering of ammonium release for nitrogen-fixing multispecies microbial cell-factories. Metab Eng. May 2014;23:154-64. doi: 10.1016/j.ymben.2014.03.002. Epub Mar. 26, 2014.

Oshikiri et al., Selective Dinitrogen Conversion to Ammonia Using Water and Visible Light through Plasmon-induced Charge Separation. Angew Chem Int Ed Engl. Mar. 14, 2016;55(12):3942-6. doi: 10.1002/anie.201511189. Epub Feb. 17, 2016.

Rhine et al., Improving the Berthelot reaction for determining ammonium in soil extracts and water. 1998. Soil Sci Soc Am J 62, 473-480. doi:10.2136/sssaj1998.03615995006200020026x.

Rodriguez et al., Stress tolerance in plants via habitat-adapted symbiosis. ISME J. Apr. 2008;2(4):404-16. doi: 10.1038/ismej.2007.106. Epub Feb. 7, 2008.

Rose et al., The Characterization of Feces and Urine: A Review of the Literature to Inform Advanced Treatment Technology. Crit Rev Environ Sci Technol. Sep. 2, 2015;45(17):1827-1879.

Rudrappa et al., Root-secreted malic acid recruits beneficial soil bacteria. Plant Physiol. Nov. 2008;148(3):1547-56. doi: 10.1104/pp.108.127613. Epub Sep. 26, 2008.

Satola et al., Metabolic characteristics of the species *Variovorax paradoxus*. Appl Microbiol Biotechnol. Jan. 2013;97(2):541-60. doi: 10.1007/s00253-012-4585-z. Epub Nov. 29, 2012.

Schneider et al., The molybdenum nitrogenase from wild-type Xanthobacter autotrophicus exhibits properties reminiscent of alternative nitrogenases. Eur J Biochem. Jun. 1, 1995;230(2):666-75.

Service., Genetically engineered microbes make their own fertilizer, could feed the world's poorest. Science. Apr. 2017; 1-9. http://www.sciencemag.org/news/2017/04/genetically-engeenered-mircobes-make-their-own-fertilizer-could-feed-worlds-poorest.

Shanmugam et al., Microbial production of ammonium ion from nitrogen. Proc Natl Acad Sci U S A. Jan. 1975;72(1):136-9.

Shokri et al., Ammonium production during the nitrogen-fixing process by wild Paenibacillus strains and cell-free extract adsorbed on nano $TiO_2$ particles. J Microbiol Biotechnol. Aug. 2010;20(8):1251-8.

Smil, Detonator of the population explosion. Nature. 1999; 400, 415 (Jul. 29, 1999).

Tilman et al., Agricultural sustainability and intensive production practices. Nature. Aug. 8, 2002;418(6898):671-7.

Tilman et al., Global food demand and the sustainable intensification of agriculture. Proc Natl Acad Sci U S A. Dec. 13, 2011;108(50):20260-4. doi: 10.1073/pnas.1116437108. Epub Nov. 21, 2011.

Torella et al., Efficient solar-to-fuels production from a hybrid microbial-water-splitting catalyst system. Proc Natl Acad Sci U S A. Feb. 24, 2015;112(8):2337-42.

Trainer et al., The role of PHB metabolism in the symbiosis of rhizobia with legumes. Appl Microbiol Biotechnol. Jul. 2006;71(4):377-86. Epub May 16, 2006.

Wiegel et al., Transfer of the Nitrogen-Fixing Hydrogen Bacterium *Corynebacterium autotrophicum* Baumgarten et al. to *Xanthobacter* gen. nov. International Journal of Systematic and Evolutionary Microbiology. 1978. 28:573-581, doi: 10.1099/00207713-28-4-573.

Wubs et al., Soil inoculation steers restoration of terrestrial ecosystems. Nat Plants. Jul. 11, 2016;2:16107. doi: 10.1038/nplants.2016.107.

Yandulov et al., Catalytic reduction of dinitrogen to ammonia at a single molybdenum center. Science. Jul. 4, 2003;301(5629):76-8.

Zhu et al., Photo-illuminated diamond as a solid-state source of solvated electrons in water for nitrogen reduction. Nat Mater. Sep. 2013;12(9):836-41. doi: 10.1038/ nmat3696. Epub Jun. 30, 2013.

Burk, The Influence of Oxygen Gas upon the Organic Catalysis of Nitrogen Fixation by Azotobacter. The Journal of Physical Chemistry. Jun. 1, 1930; 34(6): 1195-1209. doi:10.1021/j150312a006.

* cited by examiner

AMMONIA SYNTHESIS METHODS AND SYSTEMS

RELATED APPLICATIONS

This application is a national stage filing under 35 U.S.C. § 371 of international application number PCT/US2017/037447, filed Jun. 14, 2017, which claims the benefit under 35 U.S.C. § 119(e) of U.S. provisional application Ser. No. 62/358,710, filed Jul. 6, 2016, each of which is herein incorporated by reference in its entirety.

GOVERNMENT LICENSE RIGHTS

This invention was made with government support under Grant N00014-11-1-0725 awarded by the Office of Naval Research Multidisciplinary University Research Initiative, and Grant FA9550-09-1-0689 awarded by The Air Force Office of Scientific Research. The government has certain rights in the invention.

FIELD

Disclosed embodiments are related to ammonia synthesis.

BACKGROUND

Due to its use and large-scale agriculture, the reduction of $N_2$ into $NH_3$ is essential in maintaining the global geochemical nitrogen cycle and the sustainability of the human population. The most common method for producing industrial scale quantities of $NH_3$ is the industrial Haber-Bosch process. The Haber-Bosch process is efficient and scalable. However, this process consumes large volumes of natural gas as feedstock, operates at high temperature and pressure, and relies on a centralized production and subsequently transport for $NH_3$ distribution.

SUMMARY

In one embodiment, a method for producing ammonia includes: dissolving hydrogen in a solution; dissolving carbon dioxide in the solution; dissolving nitrogen in the solution; placing a glutamine synthetase inhibitor in the solution; and placing autotrophic diazotroph bacteria in the solution.

In another embodiment, a system for producing ammonia includes a reactor chamber with a solution contained therein. The solution includes dissolved hydrogen, dissolved carbon dioxide, dissolved nitrogen, a glutamine synthetase inhibitor, and autotrophic diazotroph bacteria.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
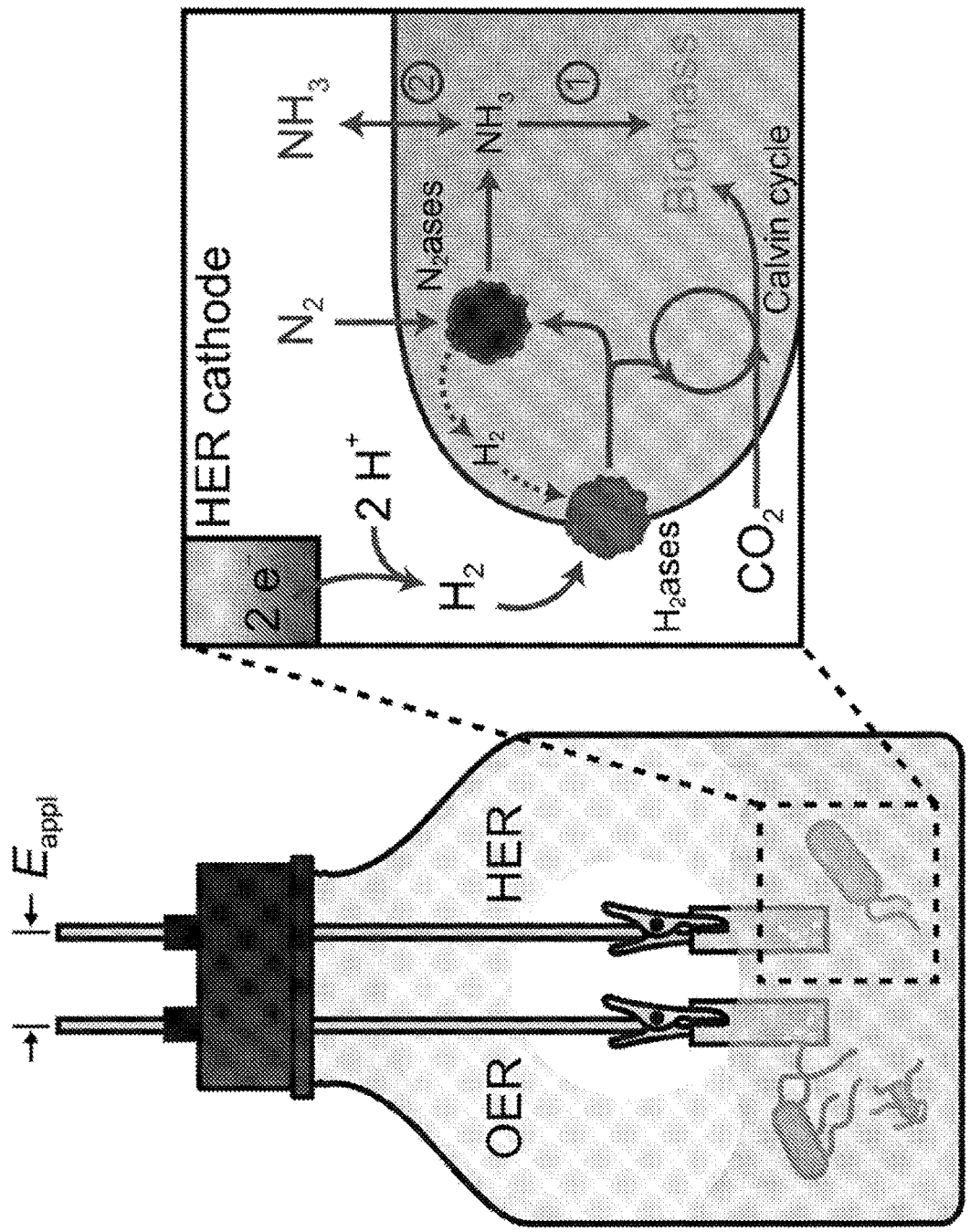
FIG. 1 is a schematic of distributed ammonia synthesis at ambient conditions within a reactor.

Unlike more traditional production methods, catalytic $NH_3$ synthesis from $N_2$ has been reported with transition metal complexes, electrocatalysts, photocatalysts, nitrogenase, and heterotrophic diazotrophs. However, these approaches typically provide limited turnovers and use sacrificial chemicals as reductants. Consequently, the Inventors have recognized that it may be desirable to enable a selective $NH_3$ synthesis from $N_2$ and $H_2O$ at ambient conditions. This may help enable a distributed approach towards $NH_3$ synthesis at ambient conditions, which may also be integrated with different forms of power including renewable energy sources. Possible benefits associated with such a production approach may include enabling on-site production and deployment of ammonia while also reducing $CO_2$ emissions as compared to more traditional production methods.

In view of the above, the Inventors have recognized the benefits associated with using a reactor-based arrangement including a solution with one or more types of bacteria that include one or more enzymes useful in the production of ammonia. Specifically, in one embodiment, a system for producing ammonia may include a reactor with a chamber containing a solution. The solution may include dissolved hydrogen, carbon dioxide, and nitrogen as well as a glutamine synthetase inhibitor in the solution. The solution may also include one or more forms of autotrophic diazotroph bacteria in the solution. During use, the autotrophic diazotroph bacteria metabolize compounds within the solution to produce ammonia. Specifically, the bacteria may include nitrogenase, such as RuBisCO, and hydrogenase enzymes that utilize nitrogen, carbon dioxide, and hydrogenase to form the desired ammonia. Appropriate autotrophic diazotroph bacteria include *Xanthobacter autotrophicus*, *Bradyrhizobium japonicum*, or any other appropriate bacteria capable of metabolizing the noted compounds to produce ammonia.

Depending on the embodiment, an inhibitor may be included in a solution to at least partially prevent the uptake of ammonia into the biomass of the bacteria. Thus, at least a portion of the ammonia produced by the bacteria may be excreted into the solution for subsequent collection. In one specific embodiment a glutamine synthetase (GS) inhibitor such as glufosinate (PPT), methionine sulfoximine (MSO), or any other appropriate inhibitor may be used.

In some embodiments, a solution placed in the chamber of a reactor may include water with one or more additional solvents, compounds, and/or additives. For example, the solution may include: inorganic salts such as phosphates including sodium phosphates and potassium phosphates; trace metal supplements such as iron, nickel, manganese, zinc, copper, and molybdenum; or any other appropriate component in addition to the dissolved gasses noted above. In one such embodiment, a phosphate may have a concentration between 9 and 50 mM.

The above noted concentrations of dissolved gases may be controlled in any number of ways including bubbling gases through the solution, generating the dissolved gases within the solution (e.g. electrolysis), or any other appropriate method of controlling the concentration of dissolved gas within the solution. Additionally, the various methods of controlling concentration may either be operated in a steady-state mode with constant operating parameters, and/or a concentration of one or more of the dissolved gases may be monitored to enable a feedback process to actively change the concentrations, generation rates, or other appropriate parameter to change the concentration of dissolved gases to be within the desired ranges noted above. Monitoring of the gas concentrations may be done in any appropriate manner including pH monitoring, dissolved oxygen meters, gas chromatography, or any other appropriate method.

In some embodiments, hydrogen may be provided to a solution using the electrolysis of water, i.e. water splitting. Depending on the particular embodiment, a power source may be connected to a first electrode and a second electrode that are at least partially immersed in a solution within a reactor chamber. The power source may correspond to any appropriate source of electrical current that is applied to the electrodes. However, in at least one embodiment, the power source may correspond to a renewable source of energy such as a solar cell, wind turbine, or any other appropriate source of current though embodiments in which a non-renewable energy source is used are also contemplated. In either case, a current from the power source is passed through the electrodes and solution to evolve hydrogen and oxygen. The current may be controlled to produce a desired amount of hydrogen and/or oxygen production at a desired rate of production. In one embodiment, the electrodes may be coated with, or formed from, a water splitting catalyst to further facilitate water splitting and/or reduce the voltage applied to the solution. For example, the electrodes may be made from one or more of a cobalt-phosphorus alloy, cobalt phosphate, cobalt oxide, cobalt hydroxide, cobalt oxyhydroxide, or any other appropriate material. In one specific embodiment, the first and second electrodes may correspond to a cathode including a cobalt-phosphorus alloy and an anode including cobalt phosphate. However, embodiments in which other types of anodes and/or cathodes are used are also contemplated as the disclosure is not so limited.

In instances where a phosphorus based anode and/or cathode is used, such as a cobalt-phosphorus alloy and/or a cobalt phosphate, a phosphate buffer may be included in the solution. Appropriate phosphates include, but are not limited to, sodium phosphates and potassium phosphates. Without wishing to be bound by theory, it is believed that during electrolysis of the water, phosphorus and/or cobalt is extracted from the electrodes. The reduction potential of leached cobalt is such that formation of cobalt phosphate from phosphate available in the solution is energetically favored. Cobalt phosphate formed in solution then deposits onto the anode at a rate linearly proportional to free cobalt phosphate, providing a self-healing process for the electrodes. A concentration of phosphate may be between 9 and 50 mM though other concentrations may also be used as the disclosure is not so limited.

In embodiments where hydrogen is produced using water electrolysis, a voltage applied to a pair of electrodes immersed in a solution may be limited to be between first and second voltage thresholds. In one such embodiment, the voltage applied to the electrodes may be greater than or equal to about 1.8 V, 2 V, 2.2 V, 2.4 V, or any other appropriate voltage. Additionally, the applied voltage may be less than or equal to about 3 V, 2.8 V, 2.6 V, 2.4 V, or any other appropriate voltage. Combinations of the above noted voltage ranges are contemplated including, for example, a voltage applied to a pair of electrodes that is between 1.8 V and 3 V. However, it should be understood that voltages both greater than and less than those noted above, as well as different combinations of the above ranges, are also contemplated as the disclosure is not so limited. For example, it is envisioned that other catalysts that enable a water splitting voltage closer to the ideal splitting voltage of 1.23 V may also be used.

As noted previously, in some embodiments, a flow of gas may be introduced to a solution contained within a reactor chamber to dissolve a desired ratio of gases in the solution. For example, in one embodiment, a system may include one or more gas sources that are fluidly connected to one or more gas inlets associated with the chamber. The gas inlets are arranged to bubble the gas through the solution. For example, a one-way valve may be fluidly connected to an inlet to the chamber bottom, a tube connected to a gas source may have an end immersed in the solution within the chamber, or the system may use any other appropriate arrangement to introduce the gases to the solution. Thus, when a gas source provides a pressurized flow of gas to the chamber, the gas is introduced into the solution where it bubbles up through the solution dissolving at least a portion of the gas therein.

While a gas source may correspond to any appropriate type of gas, in one embodiment, a gas source may provide one or more of hydrogen, nitrogen, carbon dioxide, and oxygen. Additionally, a total flow of gases provided by one or more gas sources to a solution within a reactor chamber may have any appropriate composition of gases. However, in one embodiment, a flow of gas may contain between 10 and 99.46% nitrogen, 0.04 and 90% carbon dioxide, and/or 0.5% and 5% oxygen. Of course embodiments in which a different mix of gases is bubbled through a solution including different gases and/or different concentrations both greater than and less than those noted above are also contemplated as the disclosure is not so limited.

EXAMPLES

A reactor used in the experiments included a biocompatible water splitting catalyst system including a cobalt-phosphorous (Co—P) alloy cathode for the hydrogen evolution reaction (HER) and a cobalt phosphate ($CoP_i$) anode for the oxygen evolution reaction (OER). This system enabled the use of a low driving voltage ($E_{appl}$) while producing the desired hydrogen for use in producing ammonia. Specifically, $NH_3$ synthesis from $N_2$ and $H_2O$ was accomplished using the water splitting system and driving the $N_2$ reduction reaction within $H_2$-oxidizing, autotrophic microorganisms. In this case, *Xanthobacter autotrophicus* (*X. autotrophicus*) was used. *X. autotrophicus* is a gramnegative bacterium that belongs to a small group of diazotrophs, which at micro-aerobic condition (less than about 5% $O_2$) can use $H_2$ as their sole energy source to fix $CO_2$ and $N_2$ into biomass. Therefore, in this experimental setup, electrochemical water splitting generated $H_2$ as the biological energy source and in the same reactor X. autotrophicus acted as the room-temperature $N_2$ reduction reaction catalyst to convert $H_2$ and $N_2$ into $NH_3$.

FIG. 1 shows a schematic of the experimental setup including a single-chamber reactor that houses electrodes immersed in a water solution. The electrodes included a Co—P cathode for the hydrogen evolution reaction and a $CoP_i$ anode for the oxygen evolution reaction. A gas mixture including 2% $O_2$, 20% $CO_2$, and 78% $N_2$ was bubbled through the solution at a flow rate of greater than or equal to 5 mL/min to maintain a micro-aerobic environment.

During the experiments, a constant voltage ($E_{appl}$) was applied between the OER and HER electrodes for water splitting. The hydrogenases ($H_2$ases) of X. autotrophicus oxidized the generated $H_2$, fueling $CO_2$ reduction in the Calvin cycle and $N_2$ fixation by nitrogenases ($N_2$ases). Each turnover of $N_2$ reduction yields two $NH_3$ and one $H_2$ molecule(s), the latter of which may be recycled by the hydrogenases. The generated $NH_3$ is typically incorporated into biomass, but can also diffuse extracellularly as a result of accumulation from inhibiting $NH_3$ anabolism (pathway 2) as described previously.

At the beginning of each experiment, X. autotrophicus was inoculated into the organic-free minimal medium without any nitrogen supplement. A constant driving voltage ($E_{appl}$=3.0 V) was applied to the $CoP_i$|Co—P catalyst system, and aliquots were periodically sampled for the quantification of biomass (optical density at 600 nm, $OD_{600}$) as well as fixed nitrogen (colorimetric assay).

Figure 2:
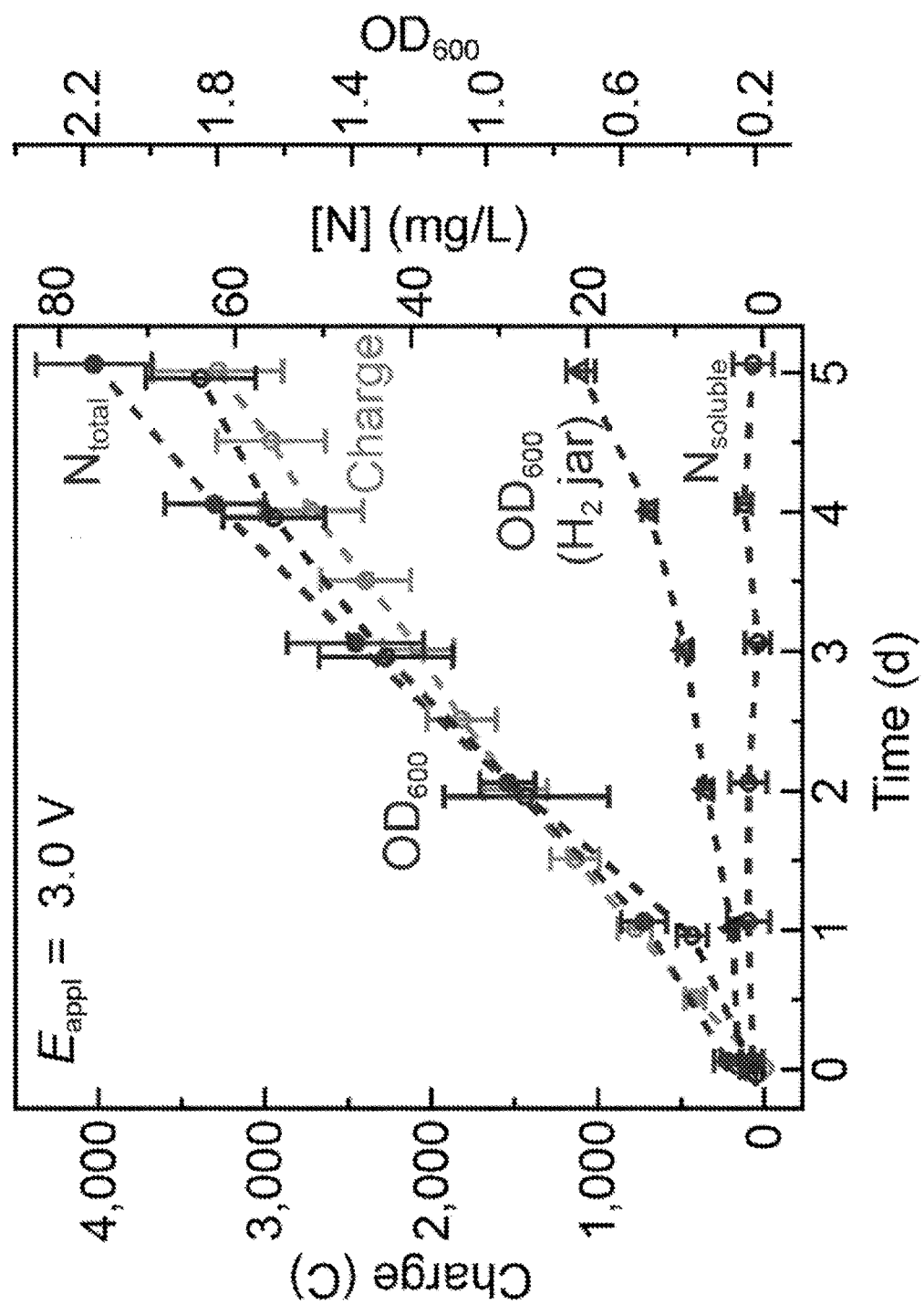
FIG. 2 is a graph of $N_2$ reduction using the CoPi|Co—P| *X. autotrophicus* catalyst system with $OD_{600}$, the amount of charge passed through, the concentration of total nitrogen content ($N_{total}$), and soluble nitrogen content ($N_{soluble}$) plotted vs. time.

The $CoP_i$|Co—P| X. autotrophicus hybrid system used electricity to reduce $N_2$, as well as $CO_2$, into biomass without sacrificial reagents. FIG. 2 presents a graph of $OD_{600}$, the amount of charge passed through, the concentration of total nitrogen content ($N_{total}$), and soluble nitrogen content ($N_{soluble}$) plotted versus the duration of the experiments. The $OD_{600}$ in a $H_2$-fermentation experiment ("$H_2$ jar") was also plotted as a comparison. The error bars in the graph denote standard error of the mean (SEM) with n≥3. As shown in the figure, the amount of charge passed into water splitting was proportional to biomass accumulation ($OD_{600}$) as well as the total nitrogen content in the medium ($N_{total}$) during the 5 day experiments.

Figure 3:
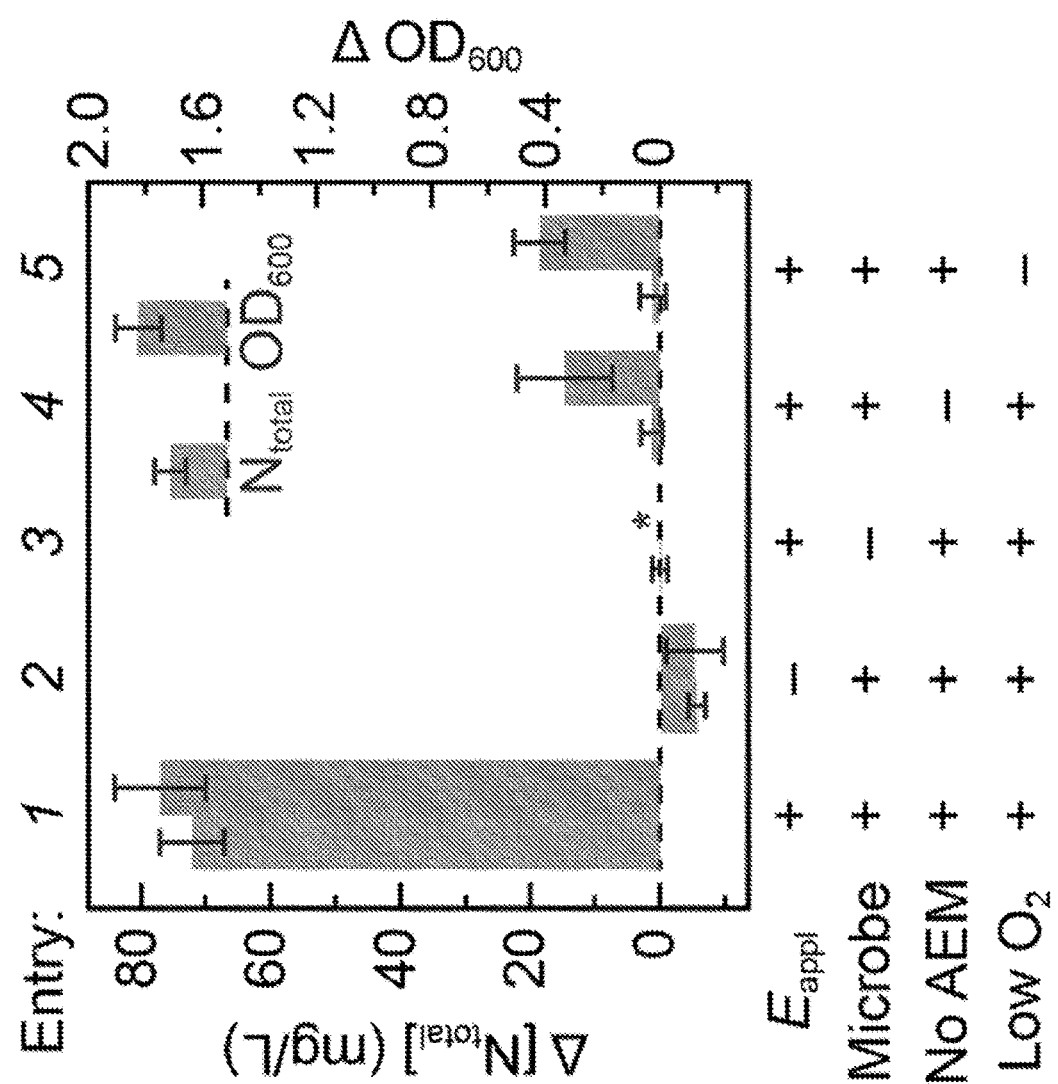
FIG. 3 is a graph of change of $N_{total}$ and $OD_{600}$ under different conditions.

FIG. 3 presents the change of $N_{total}$ and $OD_{600}$ under different experimental conditions during the 5 day experiments. As seen in the figure, the fixed nitrogen was assimilated into biomass, as there was no change in the extracellular soluble nitrogen content ($N_{soluble}$). 72±5 mg/L of $N_{total}$, as well as 553±51 mg/L of dry cell weight, accumulated continuously over the experiment (n=3, entry 1 in FIG. 3). In contrast, no accumulation of $N_{total}$ was observed in controls that omitted one of the following elements in the design: water splitting, X. autotrophicus, a single-chamber reactor, and a microaerobic environment (entry 2 to 5 in FIG. 2b). Particularly in the case of the dual-chamber experiment (entry 4 in FIG. 3), the absence of $N_{total}$ accumulation is concurrent with the increase of soluble $Co^{2+}$ concentration in the medium from 0.9±0.2 μM to 40±6 μM within 24 hours as determined by inductively coupled plasma mass spectroscopy (ICP-MS), which is close to the ~50 μM half maximum inhibitory concentration ($IC_{50}$) of X. autotrophicus. Without wishing to be bound by theory, this may indicate that the installation of an anion exchange membrane (AEM) prevented the deposition of leached $Co^+$ onto the $CoP_i$ anode, illustrating that the biocompatibility of the materials used in the system may be a desirable system property. As also illustrated in the figure, increases in $OD_{600}$ that greatly exceed increases in $N_{total}$ (entry 4 and 5 in 3) are likely due to light scattering from the accumulation of poly(3-hydroxybutyrate), which is produced as a carbon storage polymer in conditions of nutrient constraints coupled with carbon excess.

The NRR activity of the described hybrid system is also supported by whole-cell acetylene reduction assays that were done. Specifically, aliquots were sampled directly from operating devices that were exposed to an $O_2$/$H_2$/$CO_2$/Ar gas environment (2/10/10/78) and were able to reduce injected $C_2H_2$ exclusively into $C_2H_4$ at a rate of 127±33 $\mu M \cdot h^{-1} \cdot OD_{600}^{-1}$ (n=3). If the kinetic rate of $C_2H_2$ reduction by nitrogenase is one fourth of $N_2$ reduction based on the reaction stoichiometry, this activity corresponds to ~12 mg/L $N_{total}$ per day for cultures of $OD_{600}$=1.0. This $N_2$-fixing rate is consistent with the measured $N_{total}$ accumulation during the 5 day experiments and excludes the possibilities of other hypothetical nitrogen sources in conjunction with other controls (vide supra). This measurement corresponds to a NRR turnover frequency (TOF) of $1.4 \times 10^4$ $s^{-1}$ per bacterial cell. If assuming a nitrogenase copy number of about 5000 based on previous literature, this NRR TOF corresponds to roughly ~3 $s^{-1}$ per enzyme, which is consistent with previous studies. The equivalent turnover number (TON) is roughly $8 \times 10^9$ per bacterial cell and $1 \times 10^6$ per nitrogenase, at least 2 orders of magnitude higher than previously reported synthetic and biological catalysts.

Figure 4:
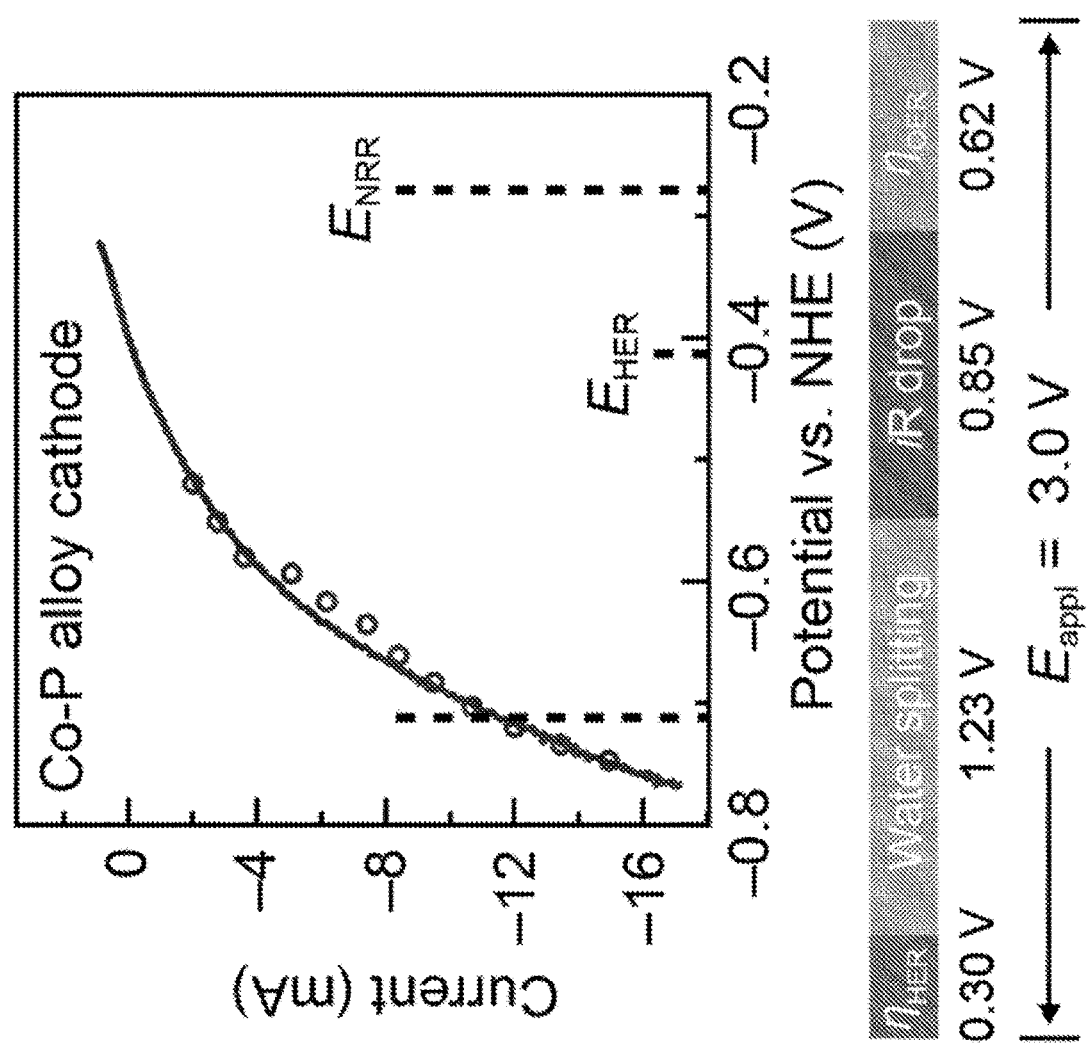
FIG. 4 is a graph of linear scan voltammetry (line, 10 mV/sec) and chronoamperometry (circle, 30 min average) of Co—P HER cathode in *X. autotrophicus* medium, iR corrected.

FIG. 4 presents the results from linear scan voltammetry (line, 10 mV/sec) and chronoamperometry (circle, 30 min average) of Co—P HER cathode in X. autotrophicus medium, iR corrected. The thermodynamic values of HER and NRR ($E_{HER}$, $E_{NRR}$) are displayed. Voltage contributions from the applied $E_{appl}$=3.0 V is shown below the I-V characterization. The NRR reaction operates with kinetic driving forces as low as 160 mV. The I-V characteristics of the Co—P HER cathode in X. autotrophicus medium indicate an apparent overpotential of about 0.43 V. Without wishing to be bound by theory, much of this value is not intrinsic to the catalytic properties of the electrodes, but originates from the build-up of a proton concentration gradient in the weakly buffered solution (9.4 mM phosphate). By subtracting the contribution of mass transport, the intrinsic NRR overpotential is about 0.16 V, much lower than previous reports in literature. The dilute medium salinity subsequently uses a driving voltage of $E_{appl}$=3.0 V, which is higher than previous reported. The low ionic conductivity contributes to about 28% of $E_{appl}$(~0.85 V), which may likely be reduced by additional optimization. Regardless, the energy efficiency of NRR ($\eta_{elec,NRR}$) in the experiments is 1.8±0.3% (n=3) during the 5 day experiments, in addition to the 11.6±1.9% electrical $CO_2$ reduction efficiency ($\eta_{elec,CO2}$, n=3). This corresponds to ~900 GJ per tonne $NH_3$, while the thermodynamic limit is 20.9 GJ per tonne $NH_3$. Based on the reaction stoichiometry of nitrogenase and upstream biochemical pathways, the theoretical number of $H_2$ molecules needed to reduce one $N_2$ molecule ranges in between 9.4~14.7, which sets an upper bound of $\eta_{elec,NRR}$ at 7.5~11.7%. Therefore, the amount of nitrogen reduction reported in this experiment is 15~23% of the theoretical yield, much higher than the faradaic efficiencies or quantum yields of other systems at ambient conditions.

The described experiments and systems exhibited faster $N_2$ reduction and microbial growth as compared to gas fermentation at similar conditions. In contrast to the observed linear growth in the hybrid system (FIG. 2), gas fermentation in the same conditions supplemented with a headspace containing ~10% $H_2$ ("$H_2$ jar" experiment in FIG. 2) shows relatively slow, nonlinear growth. This difference is dependent on $N_2$ fixation, as growth under gas fermentation and electrolysis demonstrated no discernable difference when ammonia is supplemented into the medium. Without wishing to be bound by theory, it is believed that this is the result of competitive inhibition of $H_2$ on nitrogenase, with an inhibition constant $K_{is}(D_2)$ of ~11 kPa. Where electrolysis maintains a low $H_2$ partial pressure at steady state in the hybrid device, the high $H_2$ concentration in gas fermentation may slow down the $N_2$ fixation rate and/or reduce the NRR energy efficiency. This hypothesis is supported by numerical simulations, which show slower biomass accumulation in the case of gas fermentation. Therefore, the current experiments indicate that the described hybrid device can provide additional benefits as compared to the simple combination of gas fermenters with a water-splitting electrolyzer, as the generated $H_2$ from water splitting can influence downstream biochemical pathways.

Figure 5:
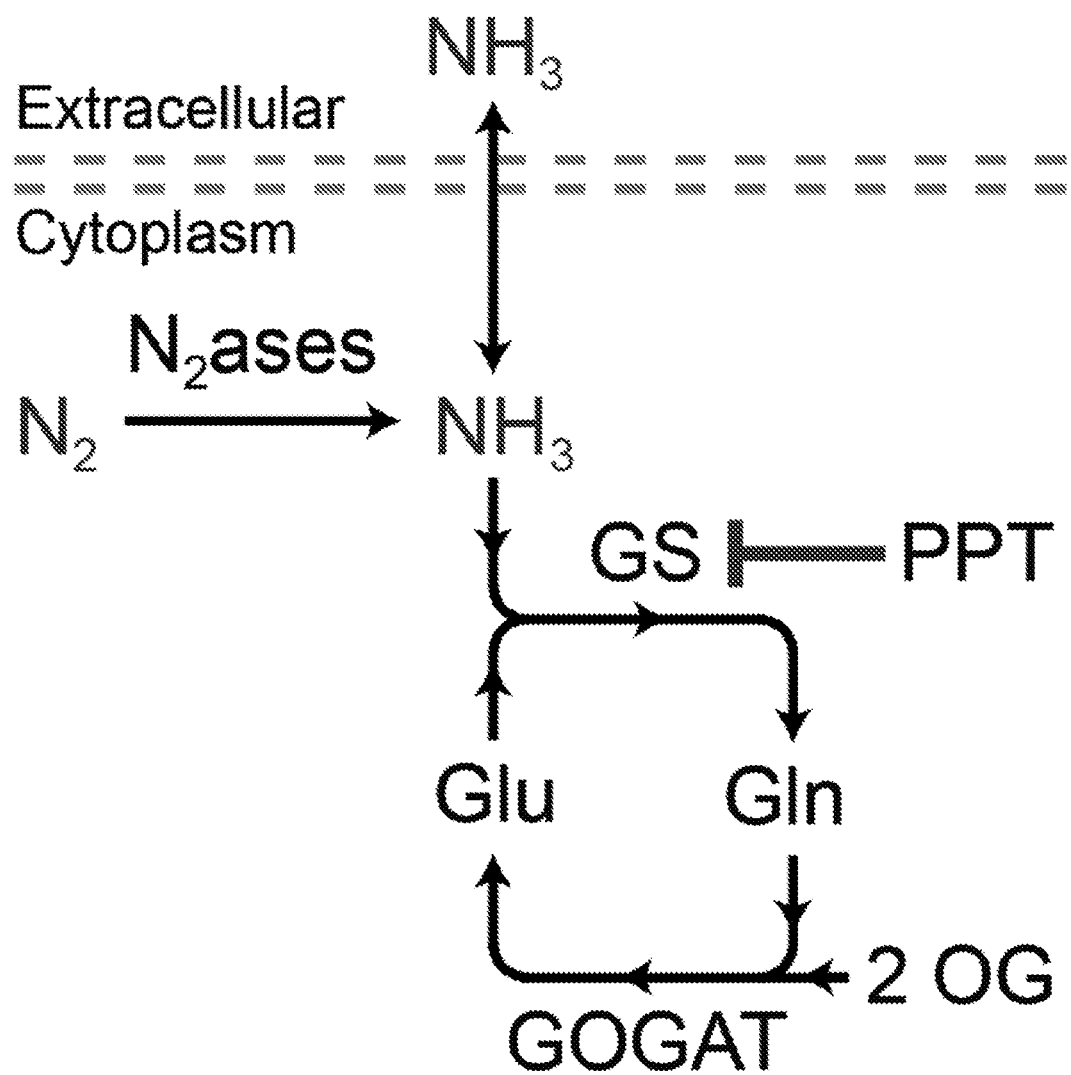
FIG. 5 Is a schematic diagram of $NH_3$ production in an extracellular media.
Figure 6:
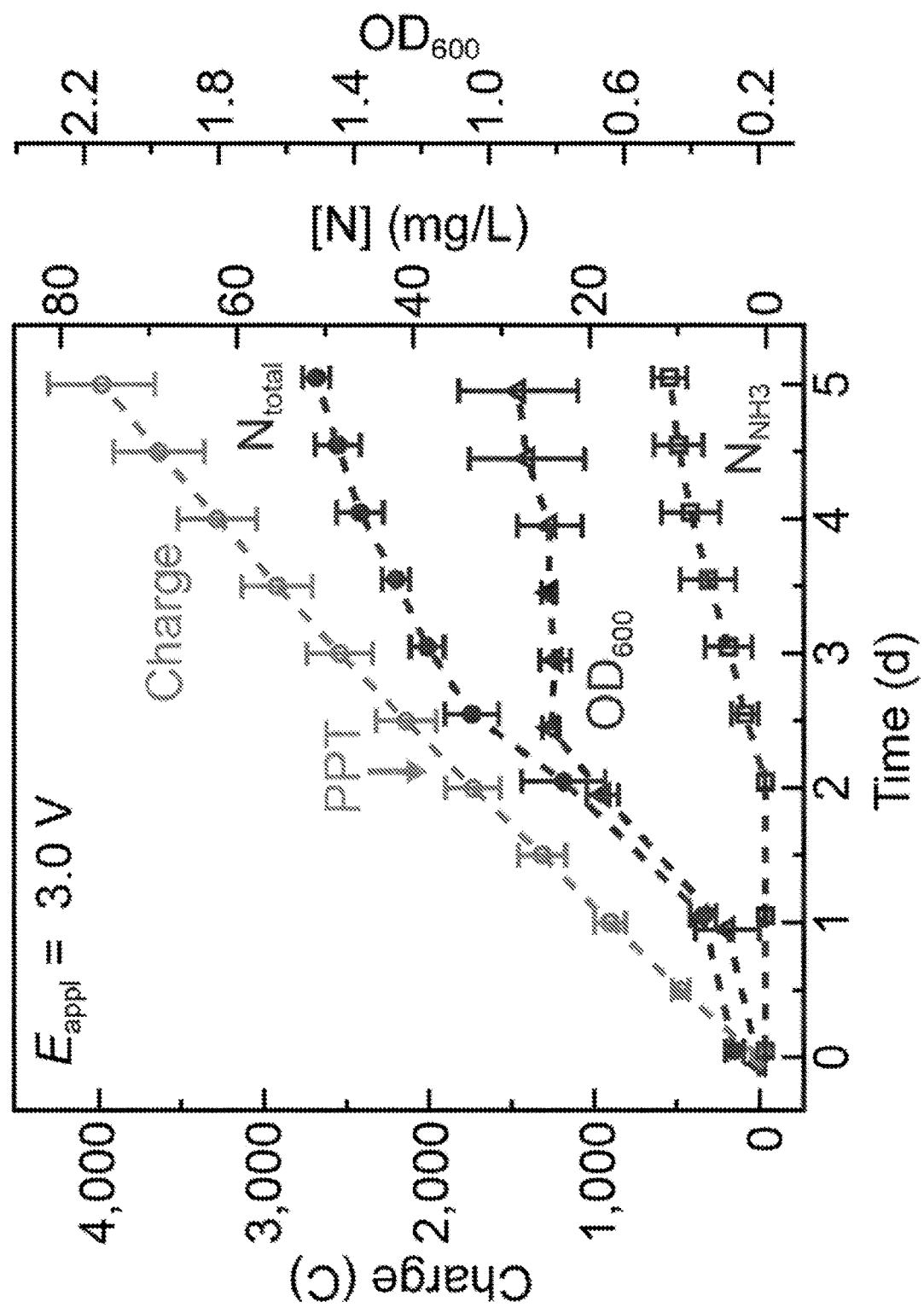
FIG. 6 is a graph of $OD_{600}$, the amount of charge passed through, the concentration of total nitrogen content ($N_{total}$) and $NH_3/NH_4^+$ extracellular content ($NH_3$) plotted against time.

The hybrid device is capable of excreting synthesized $NH_3$ into an extracellular medium. Previous biochemical assays and genome sequencing on this strain indicate that the $NH_3$ generated from nitrogenase is incorporated into biomass via a two-step process mediated by glutamine synthetase (GS) and glutamate synthase (GOGAT) (FIGS. 1 and 5). If the functionality of this $NH_3$ assimilation pathway is disrupted, direct production of an extracellular $NH_3$ fertilizer solution is realized. It has been reported that GS inhibitors can be used for $NH_3$ secretion in sugar-fementating diazotrophs. As a proof of principle, glufosinate (PPT), a specific GS inhibitor commercially used as herbicide, was used to block the $NH_3$ assimilation pathway and allow the synthesized $NH_3$ to passively diffuse out into the extracellular medium (pathway 2 in FIG. 1, and FIG. 5). After the addition of PPT, the biomass of $X$. autotrophicus stagnated, while $N_tw$ and the concentration of free $NH_3$ in the solution ($N_{NH3}$) increased (FIG. 6). This indicates that nitrogen accumulation after PPT addition mostly took the form of extracellular $NH_3$. In the end of experiments, the concentration of $N_{NH3}$ was 11±2 mg/L (~0.8 mM) and the accumulated $N_{total}$ reached 47±3 mg/L (n=3, Table S1). The rate of $N_2$ fixation tends to slow down in the latter phase of the experiments, which may be related to nitrogen regulation at transcriptional and post-transcriptional levels. Further engineering in synthetic biology is capable of alleviating this limitation.

The above experiments demonstrate the production and use of an alternative $NH_3$ synthesis approach from $N_2$, $H_2O$, and electricity. The water splitting-biosynthetic process operates at ambient conditions and can be distributed for an on-demand supply of nitrogen fertilizer. When coupled with a renewable energy supply such as a photovoltaic device of 18% energy efficiency, solar-powered $N_2$ fixation into $NH_3$ can be achieved at up to a 0.3% solar-to-$NH_3$ efficiency along with a 2.1% solar $CO_2$ reduction efficiency. A typical cropping system annually reduces ~11 g nitrogen per $m^2$, which corresponds to a ~$4\times10^5$ solar-to-$NH_3$ efficiency (assuming 2000 kWh/$m^2$ annual solar irradiance). Therefore, this approach yields a much higher efficiency and provides a sustainable route for fertilizer production without the use of fossil fuels. Though instances in which the various feeds stocks (i.e. gases) could be provided using fossil fuels as the current disclosure is not limited to only using renewable energies and/or splitting water directly in a reactor to produce the desire ammonia generation.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method for producing ammonia, the method comprising:
    dissolving hydrogen in a solution;
    dissolving carbon dioxide in the solution;
    dissolving nitrogen in the solution;
    placing a glutamine synthetase inhibitor in the solution;
    placing autotrophic diazotroph bacteria in the solution, and
    metabolizing hydrogen, carbon dioxide, and nitrogen with the autotrophic diazotroph bacteria to produce the ammonia.

2. The method of claim 1, wherein dissolving hydrogen in the solution further comprises splitting water in the solution to form hydrogen and oxygen.

3. The method of claim 1, wherein splitting water in the solution further comprises splitting water using a cathode including cobalt-phosphorus alloy and an anode including cobalt phosphate.

4. The method of claim 3, wherein the solution includes a phosphate.

5. The method of claim 1, wherein dissolving carbon dioxide and nitrogen in the solution further comprises bubbling carbon dioxide and nitrogen through the solution.

6. The method of claim 1, wherein the autotrophic diazotroph bacteria includes nitrogenase and hydrogenase enzymes.

7. The method of claim 1, wherein the autotrophic diazotroph bacteria include *Xanthobacter autotrophicus* and/or *Bradyrhizobium japonicum*.

8. The method of claim 1, wherein the glutamine synthetase inhibitor includes glufosinate (PPT) and/or methionine sulfoximine (MSO).

* * * * *

UNITED STATES PATENT AND TRADEMARK OFFICE
CERTIFICATE OF CORRECTION

PATENT NO. : 11,440,808 B2
APPLICATION NO. : 16/314979
DATED : September 13, 2022
INVENTOR(S) : Brendan Cruz Colon et al.

It is certified that error appears in the above-identified patent and that said Letters Patent is hereby corrected as shown below:

In the Claims

At Column 8, Claim 3, Line 37 please amend as follows:
3. The method of claim 2, wherein splitting water in the solution further comprises splitting water using a cathode including cobalt-phosphorus alloy and an anode including cobalt phosphate.

Signed and Sealed this
Tenth Day of October, 2023

Katherine Kelly Vidal
*Director of the United States Patent and Trademark Office*